United States Patent [19]

Yoshida et al.

[11] Patent Number: 5,850,834
[45] Date of Patent: Dec. 22, 1998

[54] RESPIRATION AIDING DEVICE

[75] Inventors: Norio Yoshida; Hiroshi Kimura, both of Ichikawa, Japan

[73] Assignee: Keytron Co., Ltd., Tokyo, Japan

[21] Appl. No.: 793,944

[22] PCT Filed: Jul. 5, 1996

[86] PCT No.: PCT/JP96/01877

§ 371 Date: Jul. 16, 1997

§ 102(e) Date: Jul. 16, 1997

[87] PCT Pub. No.: WO97/02063

PCT Pub. Date: Jan. 23, 1997

[30] Foreign Application Priority Data

Jul. 5, 1995 [JP] Japan ............................... 7-007778

[51] Int. Cl.[6] .................................................. A61M 15/08
[52] U.S. Cl. ................................ 128/204.12; 128/206.11
[58] Field of Search ......................... 128/204.12, 206.11, 128/207.18

[56] References Cited

U.S. PATENT DOCUMENTS 4,220,150  9/1980  King ..................................... 128/206.11
4,221,217  9/1980  Amezcua ............................. 128/206.11
4,753,233  6/1988  Grimes ................................. 128/207.18

FOREIGN PATENT DOCUMENTS 5-25511   4/1993  Japan .
492278    1/1976  U.S.S.R. ............................ 128/204.12

*Primary Examiner*—Aaron J. Lewis
*Attorney, Agent, or Firm*—McDermottt, Will & Emery

[57] ABSTRACT

A respiration aiding device capable of giving a little sense of incompatibility and causing no interference with respiration with no concern about coming off after a long-term use. The respiration aiding device comprises a link portion having both ends to be inserted into the right and left nares, and a pair of right and left nasal septum presser portions attached to the ends of the link portion. A dimension of the right and left nasal septum presser portions is smaller than the diameter of the nares. Magnets are mounted at opposite positions in the nasal septum presser portions so that a north pole of one magnet and a south pole of the other magnet is disposed in confronting relation to each other.

4 Claims, 4 Drawing Sheets

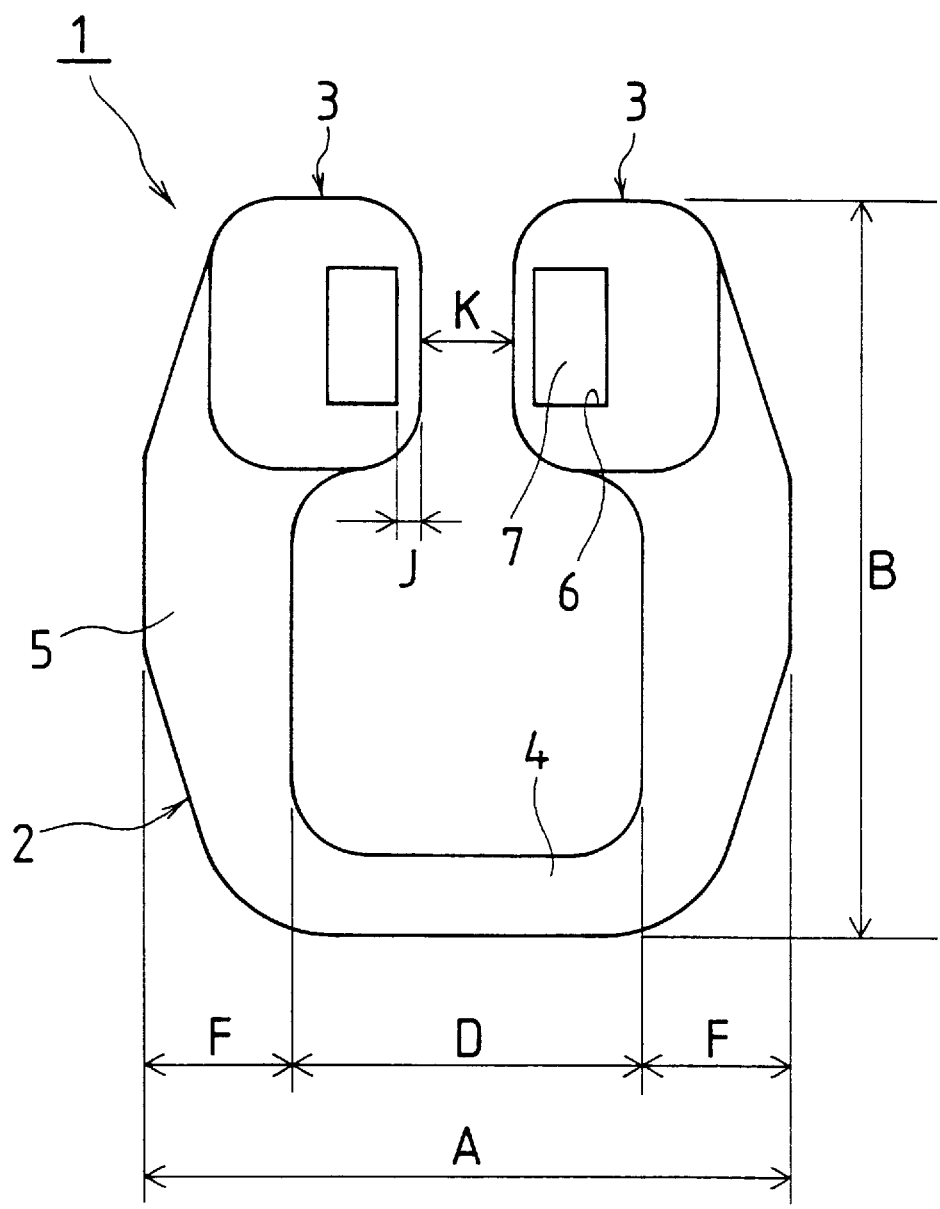

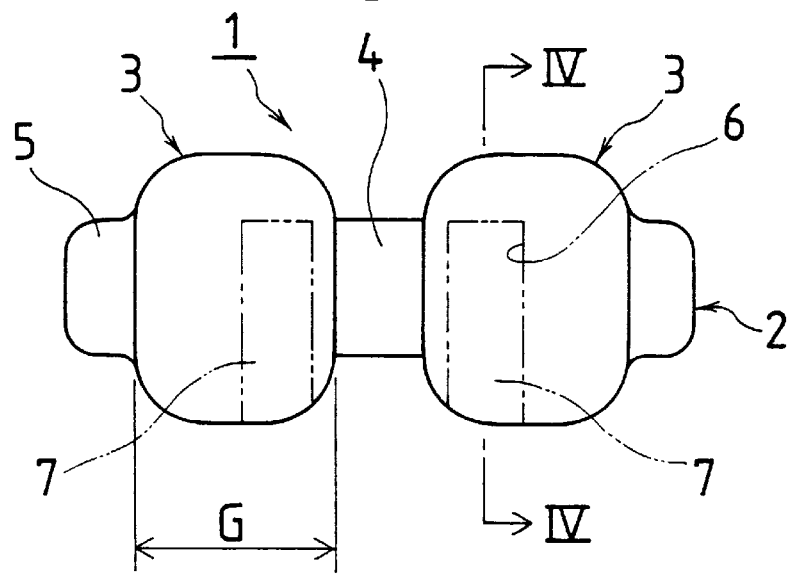
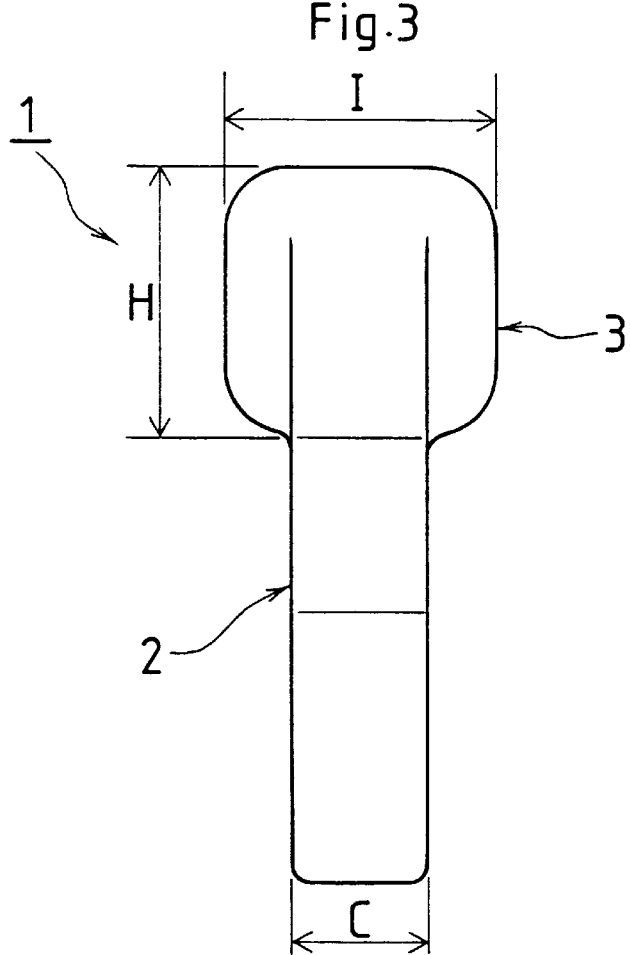

RESPIRATION AIDING DEVICE

TECHNICAL FIELD

The present invention relates to a respiration aiding device for stimulating a kinetic central nervous system (which conducts dilation and contraction of nasal meatuses) of a nose by pressuring a nasal septum, and thus expanding the nasal meatuses.

BACKGROUND ART

Iinner surface of nasal cavity is covered with a mucos membrane. Particularly, the turbinate bones located at the deep ends of the nares are abundant with venous plexuses. When the venous plexuses swell due to stipulation such as cold air, the nasal meatuses become narrow to decrease an air inflow through the nose, thus causing a respiration difficulty. When a human being lies face up with narrowed nasal meatuses, a root of a tongue plunges into a deep end of the throat and thus a passage of air is narrowed. As the air taken in through a mouth passes through the narrow passage, the relaxed soft palate vibrates to cause a snore. At this time, if the air inflow through the nose is sufficient, the snore is prevented because an intraoral soft tissue hardly vibrates.

A respiration aiding device for increasing an air inflow through the nose by expanding the nasal meatuses is helpful in increasing a quantity of oxygen uptake during exercise so as to improve an athlete's capability.

There has been proposed a respiration aiding device, as shown in FIG. 6, which comprises a U-shaped spring rod a formed in such a shape that a space between the ends thereof is a little wider than a space between the nares in a natural state, and expander portions b having a larger diameter than a spring rod a. For wearing this respiration aiding device, the expander portions b are inserted into the right and left nares while inwardly pressing the both ends of the spring rod a, and the spring rod a is released. Then, the respiration aid is retained in place by a force exerted by the spring rod a which attempts to restore its original width, and the nares are expanded outward.

However, this respiration aiding device gives a strong sense of incompatibility because the nares are forcibly expanded by the physical forces. Since the spring rod a has to possess a spring force of a certain level or higher, the diameter and rigidity thereof can not be set so small. This may result in interfering with or hindering respiration. Moreover, when the spring force of the spring rod a weakens because of repeated use, the respiration aiding device easily comes off in wearing it.

Further, as shown in FIG. 7, there is known a respiration aiding device in which presser portions d are provided at both ends of a resilient clip-like link portion c, and the right and left presser portions d abut on each other in a natural state.

With this structure, the nasal septum is caught by the right and left presser portions d by the spring force of the link portion c, working on the kinetic central nervous system for the nose by stimulating the nerves in the nasal septum so that the nasal meatuses are expanded to ease respiration. However, also in this structure, the spring force of the link portion c is utilized for retaining the respiration aiding device in the nose, and therefore the link portion c is formed relatively large in diameter and rigid. This causes an interference with respiration and can not prevent the respiration aiding device from coming off due to the weakened spring force.

DISCLOSURE OF THE INVENTION

An object of the present invention is to provide a respiration aiding device capable of making a link portion thin and soft, causing no interference with respiration, giving less sense of incompatibility when worn, with no concern about coming off after a long-term use.

A respiration aiding device of the present invention is a small appliance for assisting respiration by expanding the nasal meatuses when worn in the nares, comprising: a link portion formed into a substantial U-shape and having elasticity and both ends to be inserted into right and left nares; a pair of nasal septum presser portions formed at the both ends of the link portion; and a pair of magnets mounted at the opposite positions of said pair of nasal septum presser portions so that a north pole of one magnet and a south pole of the other magnet are disposed in confronting relation with each other. An attracting power due to magnetic forces of the pair of magnets are set so as to retain the nasal septum presser portions on both sides of a nasal septum.

The link portion and the nasal septum pressure portions may be formed with a soft elastic material. At least one of the link portion and a pair of the nasal septum pressure portions may be made of silicon resin.

The nasal septum is caught and pressured to give a stimulus by the nasal septum pressure portions inserted into the right and left nares by means of the attracting forces of the magnets mounted at the opposite positions in the nasal septum pressure portions. The link portion for linking the nasal septum presser portions hooks on to a tip of the nose when attraction between the right and left nasal septum pressure portions is out, to prevent the respiration aiding device from being drawn into the nose accidentally.

With the arrangement that the link portion and nasal septum pressure portions are formed with a soft elastic material, a soft contact with a skin can be attained in wearing and after wearing the respiration aiding device, to thus eliminate a sense of incompatibility and prevent the mucosae of the nasal cavities from being injured.

BRIEF DESCRIPTION OF THE DRAWINGS

FIG. 1 is a plan view of a respiration aiding device according to an embodiment of the present invention;

FIG. 2 is a top view of the respiration aiding device shown in FIG. 1;

FIG. 3 is a side view of the respiration aiding device shown in FIG. 1;

BEST MODE FOR CARRYING OUT THE INVENTION

Figure 4:
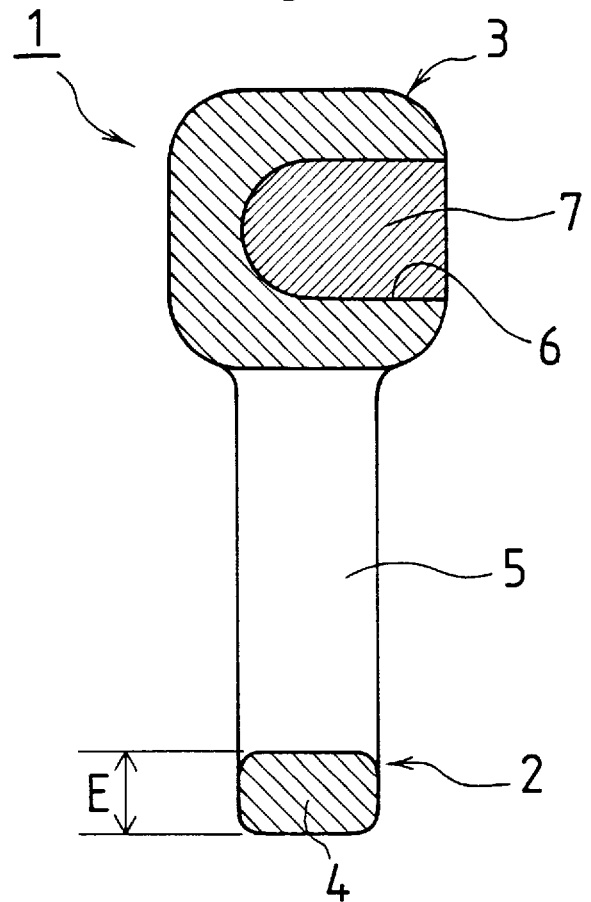
FIG. 4 is a sectional view along a line IV—IV in FIG. 2.

A respiration aiding device 1 of the present invention is made of a material which is harmless when it is in contact with a human body for a long period of time, and, as shown in FIG. 1, comprises a link porion 2 and a pair of right and left nasal septum pressing portions 3 formed at both ends of the link portion 2.

A material of the link portion 2 is relatively hard silicone rubber whose durometer-A hardness is approximately 70

(equivalent to the hardness of a tread of a vehicle tire). The link portion 2 has a bridging rod 4 spanned laterally over a tip of a nose, and a pair of right and left inserting rods 5 extending from both ends of the bridging rod 4 in the same direction perpendicularly to the bridging rod 4. Thus, the whole of the link portion 2 is formed into a substantial U-shape. The distal ends of the inserting rods 5 are bent inward. The bent ends and the intersections between the bridging rod 4 and inserting rods 5 are rounded to make an outer surface of the link portion 2 smoothly curved.

The nasal septum presser portions 3 are made of a material relatively soft silicone rubber whose durometer-A hardness is about 30 (a little harder than a rubber band), and mounted integrally on the distal ends of the insertion rods 5. Each of the nasal septum presser portions 3 has a shape of a rectangular parallelepiped with rounded and smoothly curved corners, as shown in FIGS. 2 to 4. The length I of one side of the rectangular parallelepipeds is set a little longer than the width C of the link portion 2, when viewed laterally.

As shown in FIGS. 2 and 4, insertion holes 6 are formed near opposite surfaces of the right and left nasal septum presser portions 3 in such a way that the insertion holes 6 extend from surfaces crossing the opposite surfaces to a depth of ⅔ or more of the depth of the presser portions 3, and magnets 7 are fitted into the insertion holes 6.

The right and left magnets 7 are mounted so that a north pole of one magnet and a south pole of the other magnet are disposed in confronting relation to each other to attract each other. As described later, magnets having strength of approximately 120 gauss are used as the magnets 7 so that a pain is not felt when the magnets 7 catch the nasal septum between them and so that sufficient attracting forces are produced to retain the right and left nasal septum presser portions 3 on both sides of the nasal septum.

With the arrangement of magnets embedded in the nasal septum presser portions 3, and the arrangement that the outer surfaces of the nasal septum presser portions 3 and link portion 2 are smoothly curved, no irregularity is formed on the surface of the nasal septum presser portions 3, to prevent the mucous membrane of the nasal cavities from being injured and facilitate cleaning of the whole aiding device.

In order to alleviate discomfort which may be experienced when wearing the respiration aiding device 1, a size of each portion is a very important factor, and it is generally defined as described below.

The width A of the respiration aiding device 1 is in a range of 13–15 mm, and the length B thereof is in a range of 15–17 mm. The width C of the link member 2 is approximately 3 mm. The length D of the bridging rod 4 is in a range of 7–8 mm, and the thickness E thereof is in a range of 1.5–2 mm. The thickness F of the insertion rods 5 is preferably approximately 3 mm. The thickness G of the nasal septum presser portions 3 is in a range of 4–5 mm, the length H thereof is approximately 6 mm, and the width I thereof is approximately 6 mm. These dimensions, however, need be slightly adjusted, depending on whether the device is worn by an adult or child, or a female or male, or depending on an individual difference.

The covering depth J from the opposite surfaces of the nasal septum presser portions 3 to the magnets 7 is set to a very small value of approximately 0.5 mm, so that the attracting forces of the magnets 7 is not adversely affected. When no magnetic force is acting, the distance K between the opposed surfaces of the nasal septum presser portions 3 is approximately 2 mm.

For showing the size of the respiration aiding device 1, the drawings show the shape of the device assuming that no magnetic force of the magnets 7 acts. Actually, the right and left magnets 7 attract each other, to make the opposite surfaces of the right and left nasal septum presser portions 3 be in contact with each other.

The respiration aiding device 1 is worn as described below.

The distal ends of the link portion 2 are parted from each other with fingers in order to form a space between the opposite surfaces of the right and left nasal septum presser portions 3. The both ends of the link portion 2 and the right and left nasal septum presser portions 3 are inserted into the right and left nares, respectively.

Figure 5:
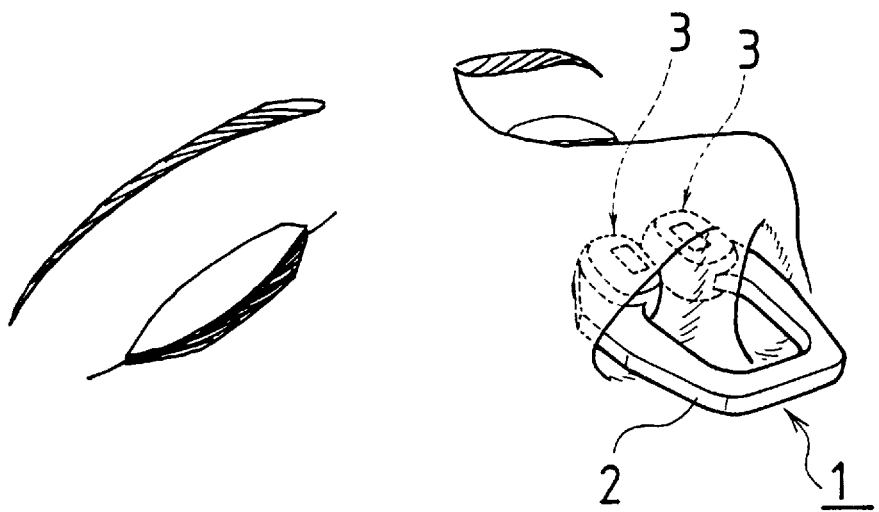
FIG. 5 is a perspective view of the respiration aiding device shown in FIG. 1 in a wearing state.
Figure 6:
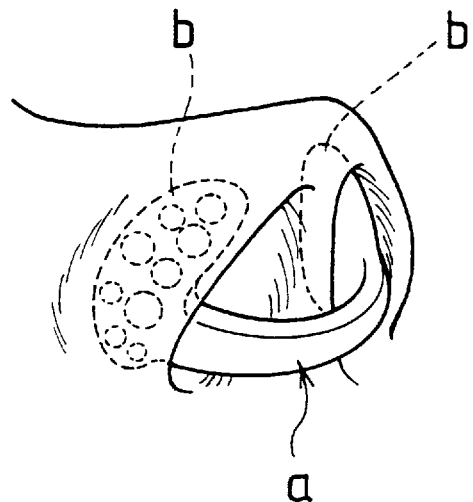
FIG. 6 is a perspective view of a conventional respiration aiding device.
Figure 7:
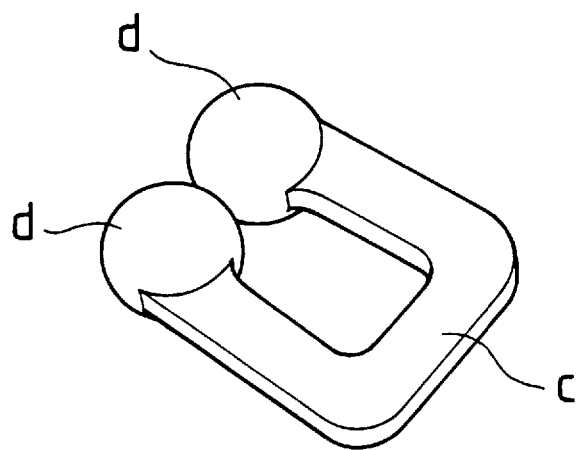
FIG. 7 is a perspective view of another conventional respiration aiding device.

Then, when the fingers are released from the link portion 2, the right and left nasal septum presser portions 3 attract each other with the nasal septum therebetween by means of the magnetic forces of the embedded magnets 7, as shown in FIG. 5, thereby pressing the nasal septum to stimulate it appropriately.

The stimulation is transmitted to a brain to work on the kinetic central nervous system for the nose, so that the nasal meatuses are expanded to increase a quantity of breathing air.

Although there has been described what is considered to be the preferred embodiment, the forms of the respective portions of the respiration aiding device 1 are not limited to those illustrated.

The link portion 2 as well as the nasal septum presser portions 3 can be formed with a soft elastic material. In this case, a shape-retaining property of the link portion 2 may be poor. However, as the nasal septum presser portions 3 are retained on both sides of the nasal septum by means of the magnetic forces, there is no serious problem in practice.

A material of the respiration aiding device 1 may be any elastomer other than silicone rubber as long as it is harmless to a human body and has appropriate elasticity.

Silicone rubber is easy to be charged with static electricity. When a respiration aiding device made of silicone rubber is worn, it is rubbed by an air flowing in and out in respiration to be charged with static electricity. As a result, harmful particles contained in the air passing through the nasal meatuses can be adsorbed and removed to conduct health.

According to the present invention, when the respiration aiding device is worn by catching the nasal septum with the right and left nasal septum presser portions, the kinetic central nervous system for the nose is stimulated to expand the nasal meatuses, increasing the quantity of air flowing in through the nose in respiration. This takes effects of suppressing nasal congestion caused by light rhinitis or the like and of activating the cardiopulmonary functions and metabolism during exercise. Moreover, since respiration is eased, a snore is suppressed.

Since the right and left nasal septum presser portions attract each other by the magnets embedded therein, the link portion can be formed more thinly and softly in comparison with a respiration aiding device to be worn by means of the spring force of the link portion. This leads to little sense of incompatibility in wearing the respiration aiding device. Moreover, even after the respiration aiding device is used for a long period of time, it is unnecessary to concern about lowering of the attracting forces.

As the respiration aiding device according to the present invention comes into contact with a skin softly, it provides a less sense of incompatibility in wearing and is accompanied with a little risk of injuring the mucosae, in comparison with a respiration aiding device which is entirely formed with a hard elastic member.

Furthermore, as the respiration aiding device adsorb and remove particles from the breathing air by an electrostatic effect, it enables more healthy jogging in an urban area.

We claim:

1. A respiration aiding device, comprising:
   a link portion formed into a substantial U-shape and having elasticity and both ends thereof adapted to be inserted into right and left nares;
   a pair of nasal septum presser portions formed at the both ends of said link portion and comprising substantially flat surfaces adapted to press against opposing sides of a nasal septum; and
   a pair of magnets mounted at opposing positions of said pair of nasal septum presser portions so that a north pole of one magnet and a south pole of the other magnet are disposed in confronting relation with each other,
   wherein the attracting power due to magnetic forces of said pair of opposing magnets are set so as to retain said nasal septum presser portions on both sides of a nasal septum.

2. A respiration aiding device according to claim 1, wherein at least one of said link portion and said pair of nasal septum presser portions are made of silicone resin.

3. A respiration aiding device according to claim 1, wherein said link portion and said pair of nasal septum presser portions are formed with a soft elastic material.

4. A respiration aiding device according to claim 3, wherein at least one of said link portion and said pair of nasal septum presser portions are made of silicone resin.

* * * * *